United States Patent [19]

Davis et al.

[11] Patent Number: 4,520,702
[45] Date of Patent: Jun. 4, 1985

[54] INSPECTION AND CUTTING APPARATUS

[75] Inventors: Walter L. Davis, Milton-Freewater, Oreg.; Dale Messenger, Montgomery, Ala.; Malcolm W. Randall, Milton-Freewater, Oreg.

[73] Assignee: Key Technology, Inc., Milton-Freewater, Oreg.

[21] Appl. No.: 496,992

[22] Filed: May 27, 1983

Related U.S. Application Data

[63] Continuation-in-part of Ser. No. 388,138, Jun. 14, 1982, abandoned.

[51] Int. Cl.³ .............................................. B26D 5/34
[52] U.S. Cl. .......................................... 83/71; 83/289; 83/303; 83/337; 83/364; 83/371; 356/237
[58] Field of Search ..................... 234/50; 83/71, 286, 83/289, 364, 365, 371, 337, 338, 303; 209/580, 587; 356/237

[56] References Cited

U.S. PATENT DOCUMENTS

| | | | |
|---|---|---|---|
| 3,059,842 | 10/1962 | Wadey | 234/50 |
| 3,543,035 | 11/1970 | Raye et al. | 250/223 |
| 3,664,397 | 5/1972 | Raye et al. | 83/71 X |
| 3,844,091 | 10/1974 | Veduik | 83/337 X |
| 4,114,488 | 9/1978 | Vornfett | 83/371 X |
| 4,147,619 | 4/1979 | Wassmer | 209/587 |
| 4,186,836 | 2/1980 | Wassmer | 209/587 X |
| 4,246,098 | 1/1981 | Conway et al. | 209/587 X |

Primary Examiner—James M. Meister
Attorney, Agent, or Firm—Wells, St. John & Roberts

[57] ABSTRACT

An article inspection and cutting apparatus (10) is described for high production processing of elongated articles (12) such as raw potato strips (french fries). The apparatus includes a conveyor (20) for moving the articles (12) in line in a large number of transversely spaced lanes past an inspection (28) station and a cutting station (30). Scanning cameras (38, 40) at the inspection station (28) rapidly scan across the lanes to detect color or shade variation in the articles (12) and generate electrical signals characteristic of the defect. Rotating sets of knife wheels (54) are positioned at the cutting station for selectively projecting two or more knives (68) from the periphery of the wheel to cut sections of the article (12) containing the defect to separate the defective portion from the remainder of the article. The apparatus 10 has the capability of detecting the size of different shade defects and removing smaller dark defects and larger lighter defects.

19 Claims, 25 Drawing Figures

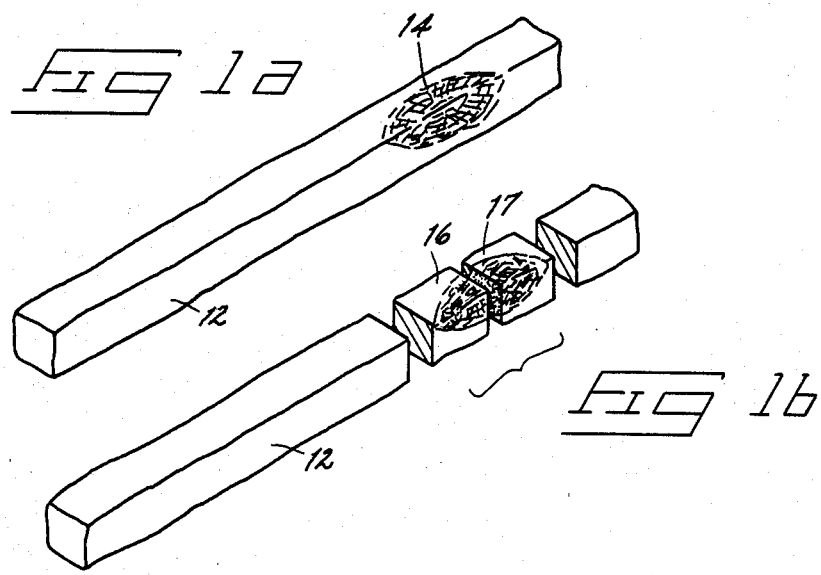
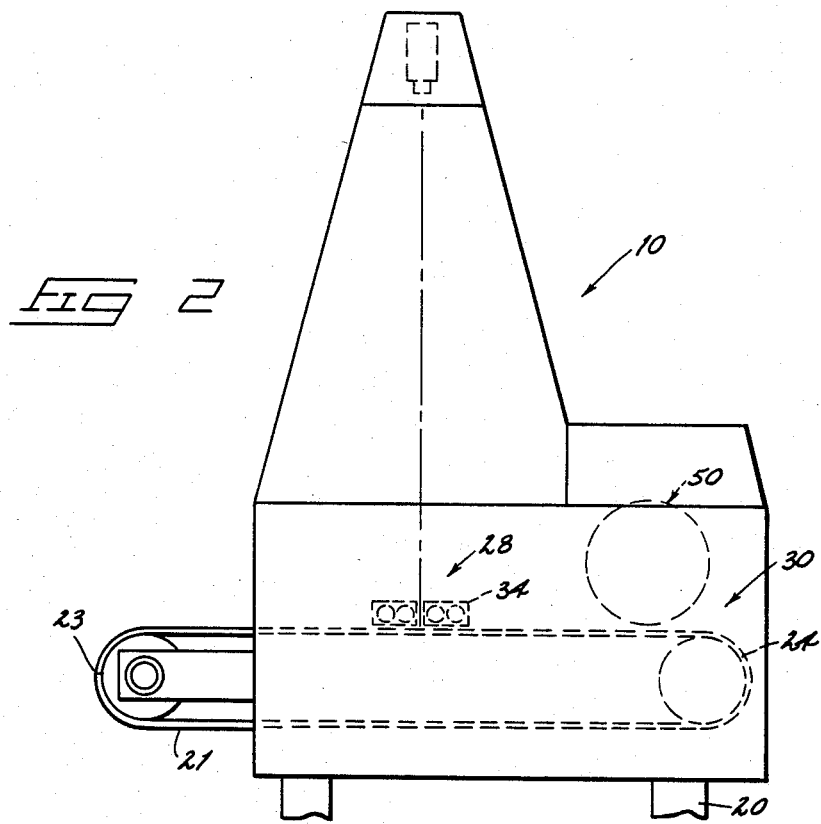

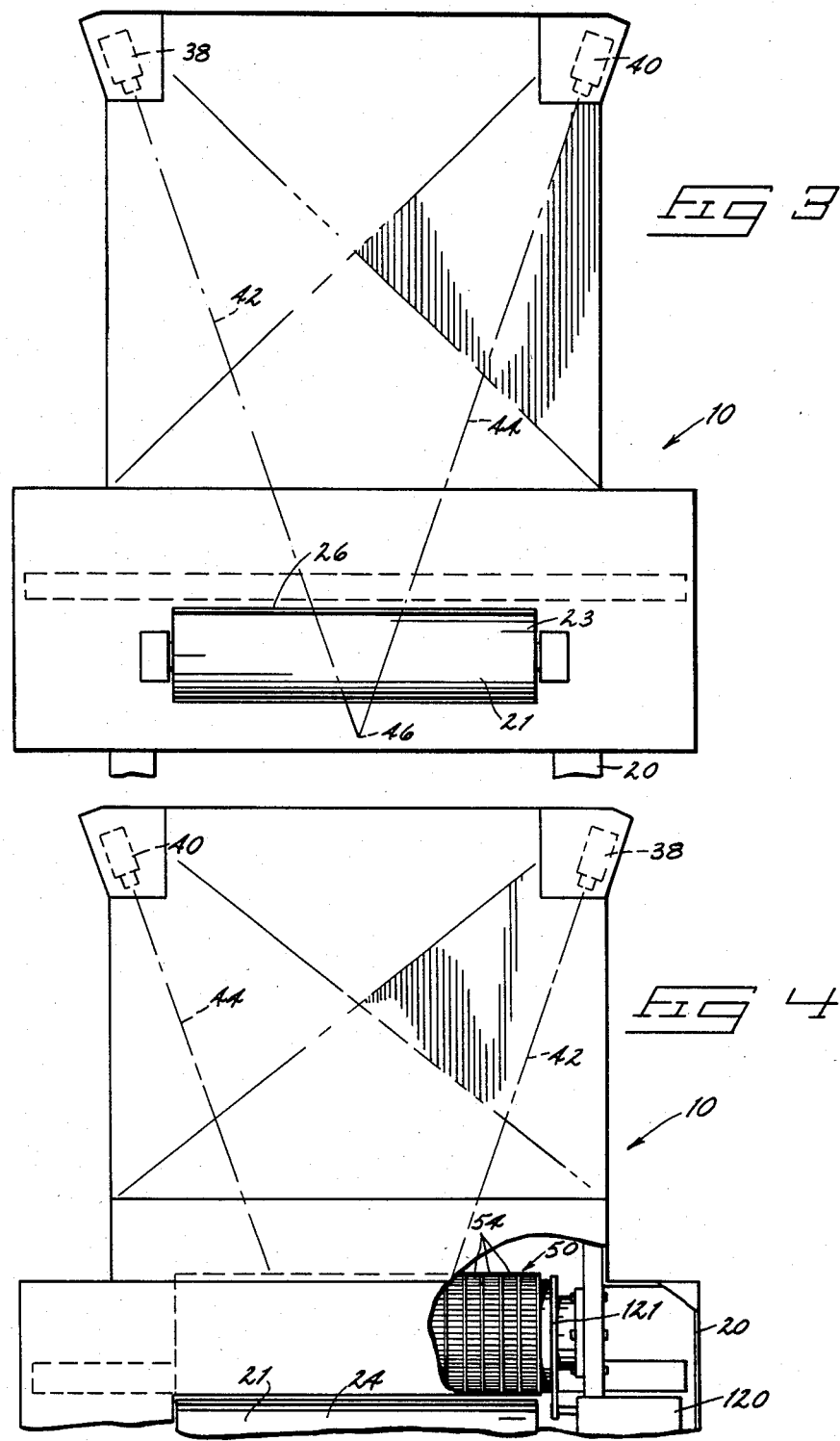

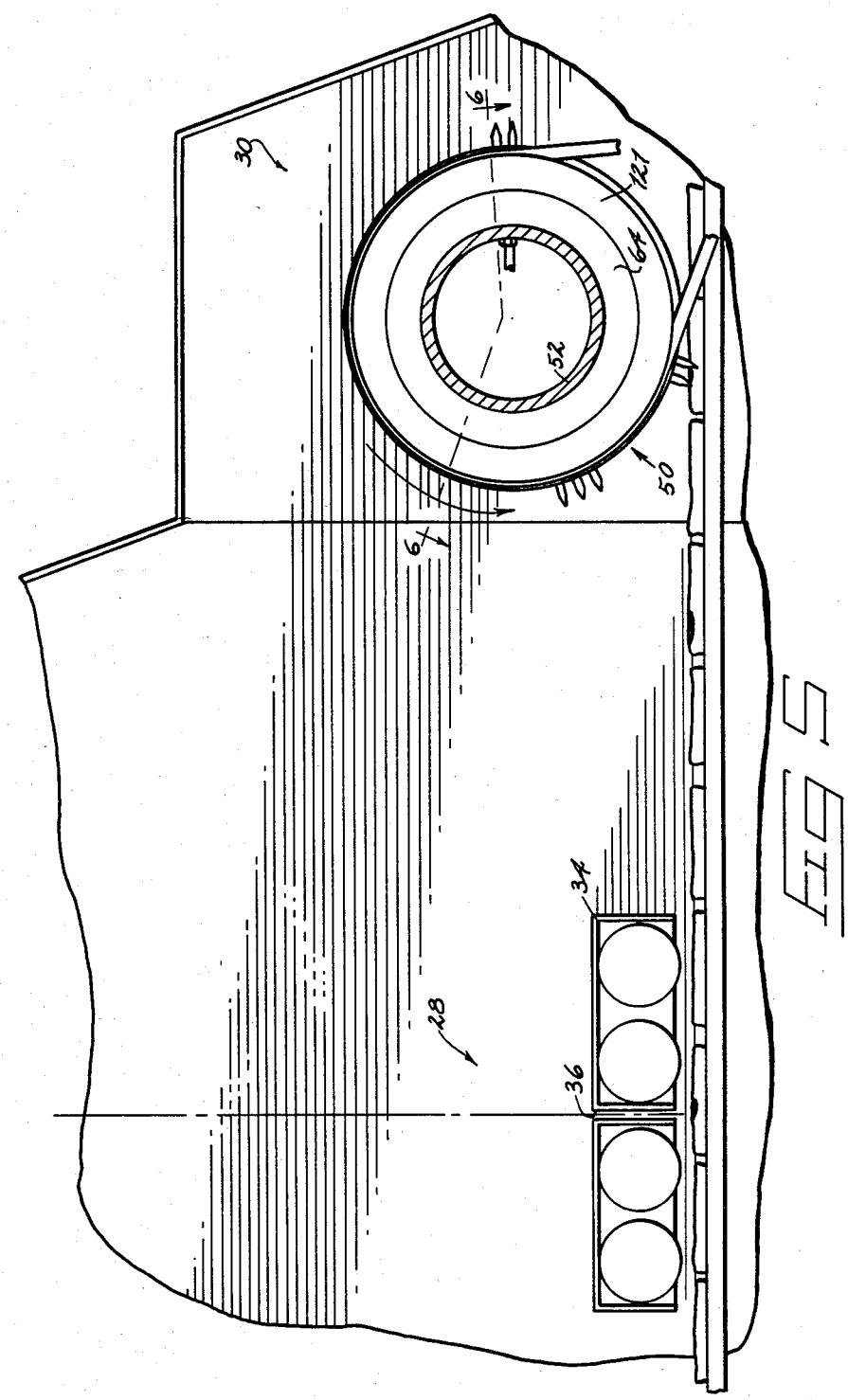

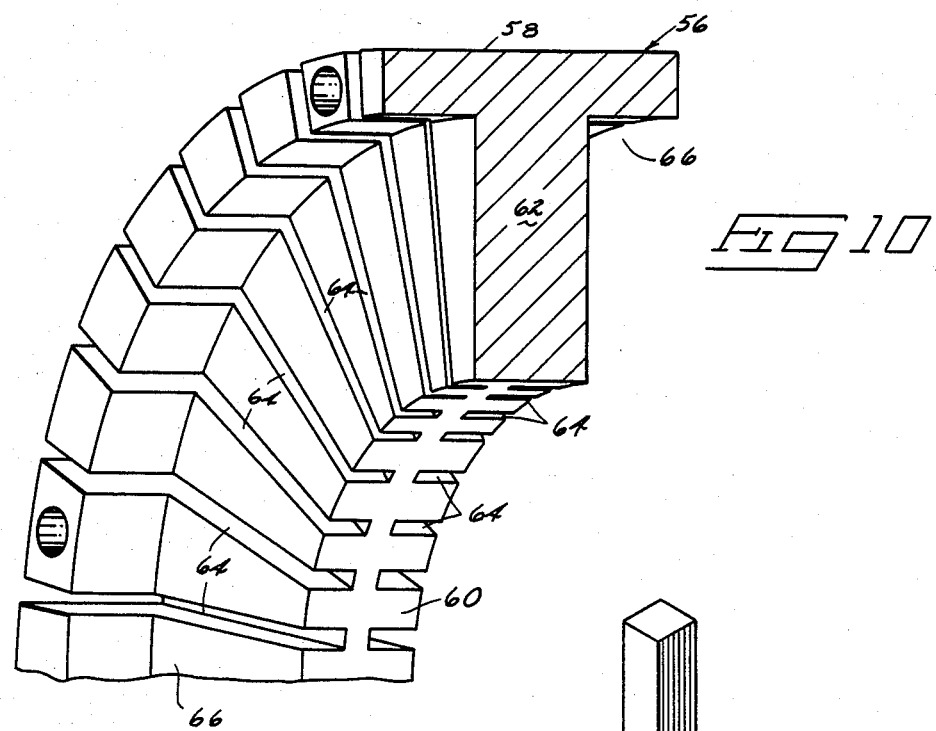
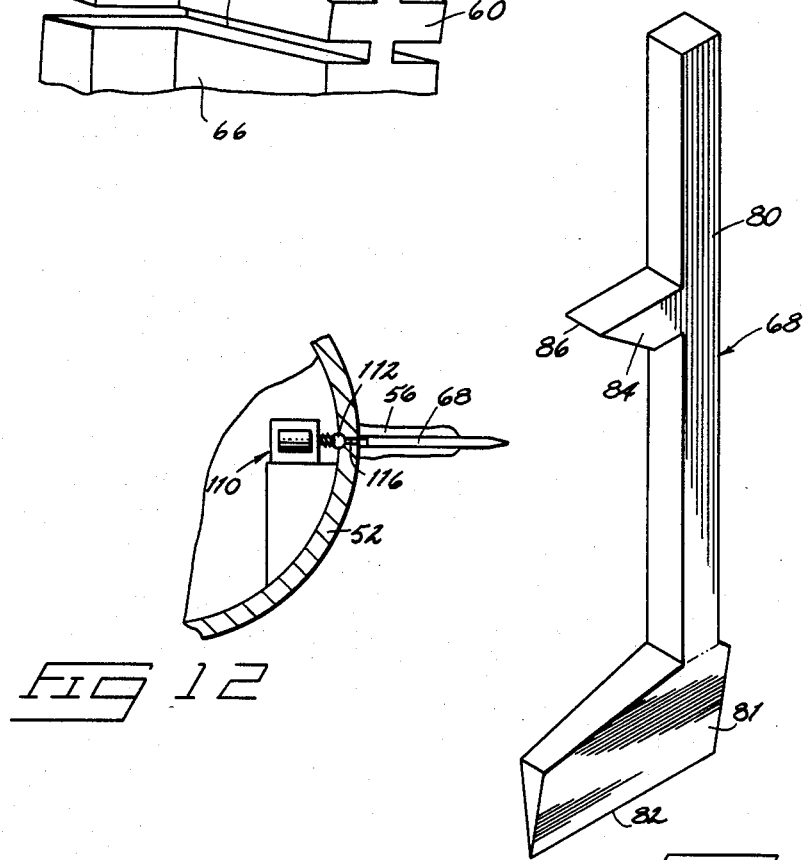

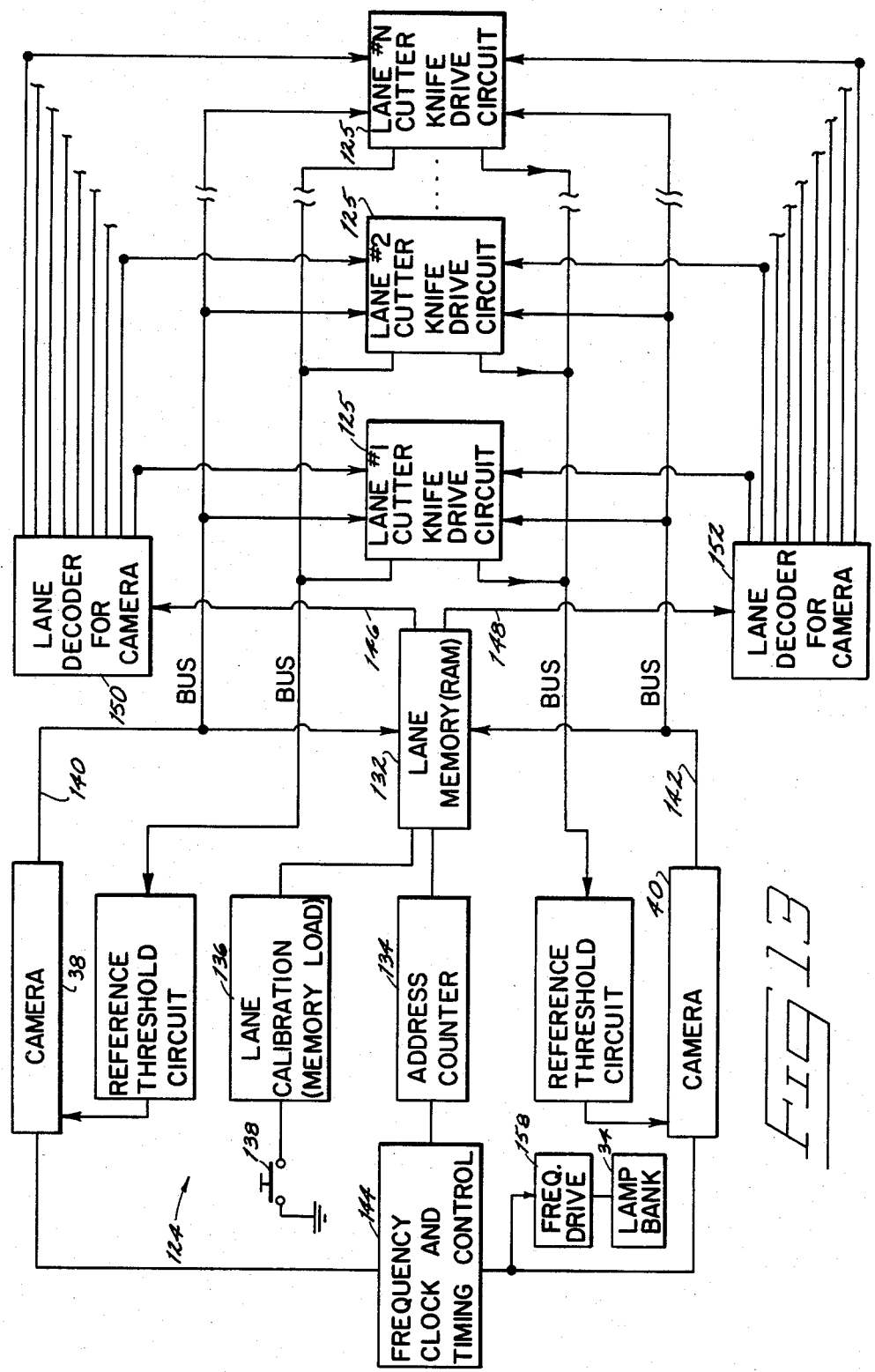

R₁ = SHADE #1 THRESHOLD (LIGHT)
R₂ = SHADE #2 THRESHOLD (DARK)

INSPECTION AND CUTTING APPARATUS

RELATED APPLICATIONS

This is a continuation-in-part application to a parent application S/N 388,138 filed June 14, 1982, now abandoned, entitled "Inspection and Cutting Apparatus. Such parent application was abandoned after this application was filed.

TECHNICAL FIELD

This invention relates to inspection and cutting equipment for detecting defects in elongated articles and for cutting the defects from the articles as the articles are being processed in a high production facility.

BACKGROUND OF THE INVENTION

Many attempts have been made to devise a high production system for detecting defects in elongated articles such as raw potato strips and the like and for removing the defects as the articles are being processed. Many systems have been constructed for optically inspecting the articles and for separating the articles based upon whether or not the optical information indicates that the article contains a defect. Frequently the size of the defect may be quite small and the remainder of the article may be quite satisfactory. Additional processing of the article to remove the defect requires additional equipment and additional handling which increases the costs of processing.

Attempts have been made to process elongated articles such as elongated sliced potatoes utilized for frozen "french fries" in which the elongated articles are aligned in transversely spaced lanes and passed beneath individual lane electro-optical cameras for inspecting the french fries for defects. If defects are encountered, one or more knives on a rotating wheel is projected from the wheel to cut the defect from the article. One such device is illustrated in U.S. Pat. Nos. 3,543,035 and 3,664,337 granted to Raye et al on Nov. 24, 1970 and May 23, 1972 respectively. Because of limitations of the equipment, it is very difficult to process large volumes utilizing the equipment illustrated in such patents. An important limitation is the difficulty of positioning and processing the elongated potato strips in very close proximity to each other and for moving the articles past the electro-optical inspection station and the wheel cutting station at high speeds.

Along a similar line, U.S. Pat. No. 4,114,488 granted Sept. 19, 1978 to Karl Ulrich Vornfett describes an apparatus for moving raw potato sticks past sensing equipment for sensing whether or not sticks have defects and then past a cutting system having a pair of vertically movable cutters that move down through a slot in a trough conveyor for cutting out the defect with the defect segment being removed below the trough. Such a system is quite slow and incapable of handling high volume production. As the knife blades pass down through the product, the product remains substantially stationary and cannot regain its forward movement until the knives are retracted.

Of general background importance is the equipment described in U.S. Pat. No. 4,186,836 granted Feb. 5, 1980 to Norman B. Wassmer et al. Such a system is directed to a sorting apparatus for placing potato segments uniformly on a conveyor bed in substantially a one layer configuration and passing the conveyor bed of segments underneath scanning electro-optical cameras for detecting defects or dark spots on the potato pieces. Vacuum nozzles downstream of the scanning cameras are then activated for picking up and sorting the defective articles from the nondefective articles. Although such a system is capable of sorting product on a large volume basis, it is not concerned with removing the defects from the remainder of the product.

One of the principal objects of this invention is to provide high volume, accurate inspection and cutting equipment for detecting color or shade variance defects in elongated articles such as potato sticks or strips and then removing the defects while the sticks or articles are moving.

A still further object of this invention is to provide high volume inspection and cutting apparatus for removing defects from elongated articles with equipment that is quite inexpensive relative to its capacity.

These and other objects and advantages of this invention will become apparent upon reading the following detailed description of a preferred embodiment.

BRIEF DESCRIPTION OF PREFERRED AND ALTERNATE EMBODIMENTS

Preferred and alternate embodiments of this invention are illustrated in the accompanying drawings, in which:

FIG. 1a is an isometric view of a blemished raw potato strip before the blemished portion is removed;

FIG. 1b is an isometric view similar to FIG. 1A except showing the strip cut with the blemished portion cut from the unblemished portions;

FIG. 2 is a side elevation view of an inspection and cutting apparatus designed to detect the blemish illustrated in FIG. 1A and to cut the blemish from the remainder of the section as illustrated in FIG. 1b on a high volume basis;

FIG. 3 is a front view of the apparatus illustrated in FIG. 2;

FIG. 4 is a rear view of the apparatus illustrated in FIG. 2 showing a breakaway section illustrating a portion of a cutting wheel assembly;

FIG. 5 is an illustrative fragmentary longitudinal view of the inspection and cutting apparatus illustrating a lane of elongated articles passing sequentially in line past an inspection station for detecting defects in the articles and then past a cutting section for cutting sections from the articles containing the defects;

Figure 8:
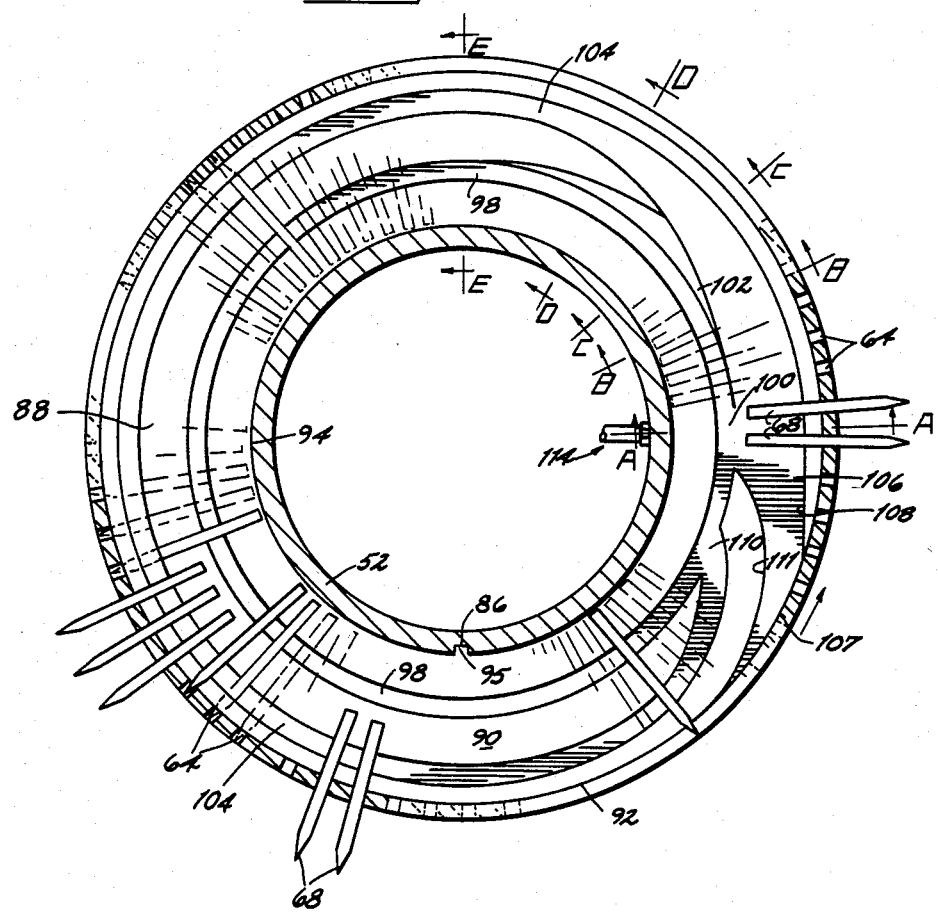
FIG. 8 is a radial cross-sectional view taken along line 8—8 in FIG. 6 illustrating the relative position of the knives in relation to a stationary track member for guiding the knives in radial directions as the knives are rotated about the center axis of the wheel assembly.
Figure 14:
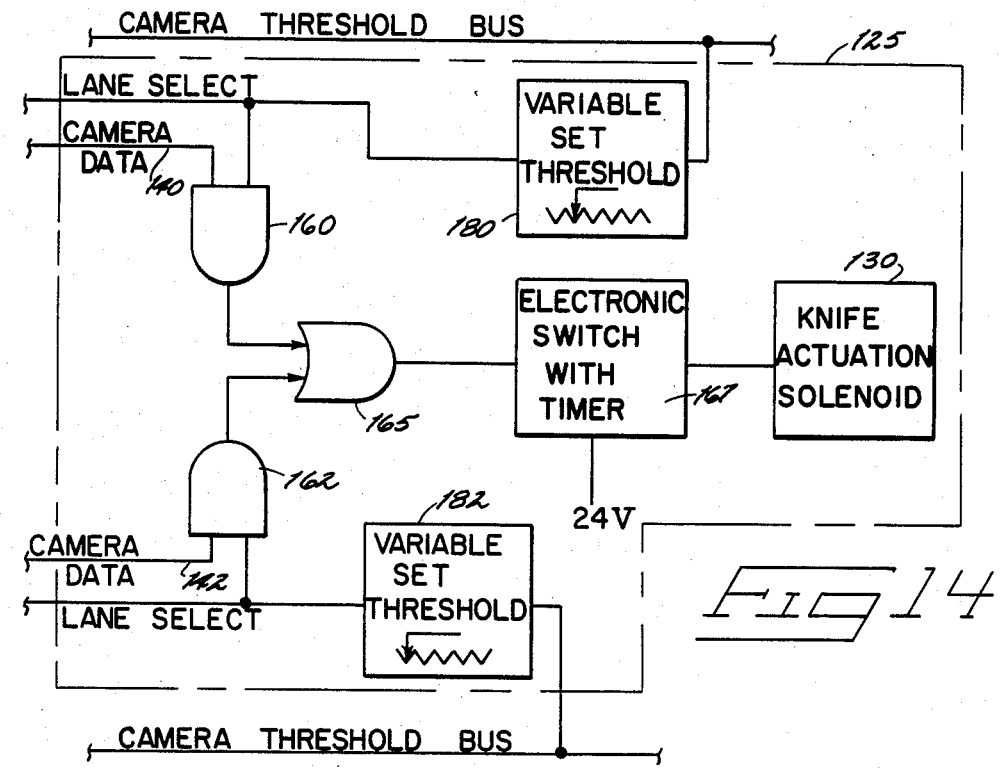
Figure 15:
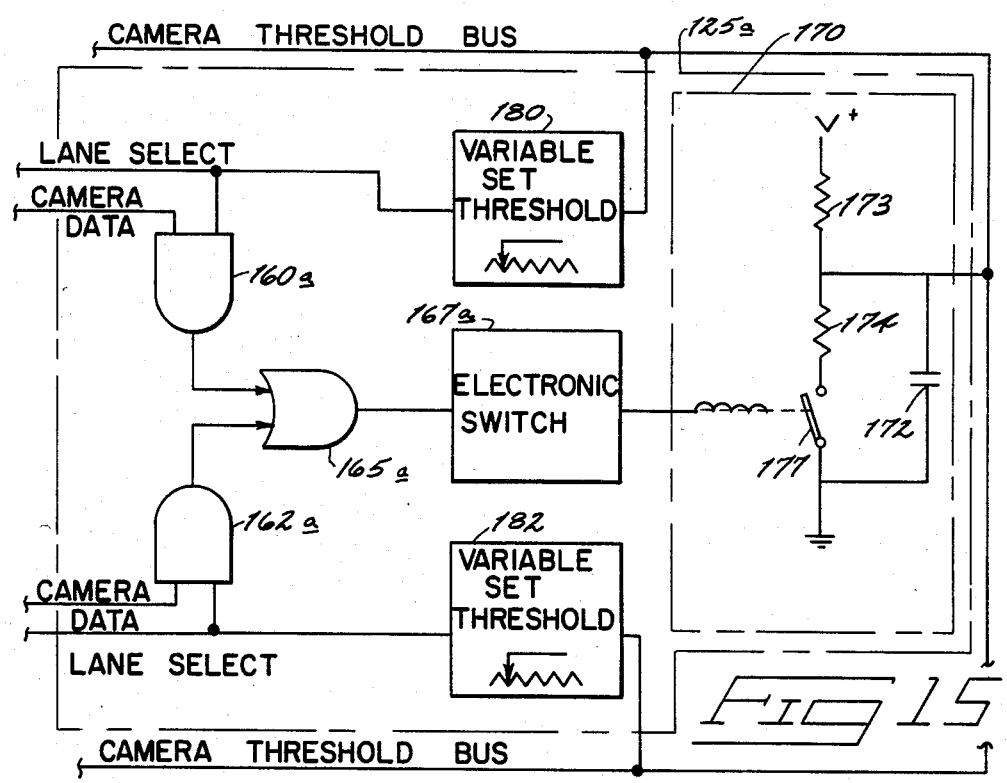
Figure 16:
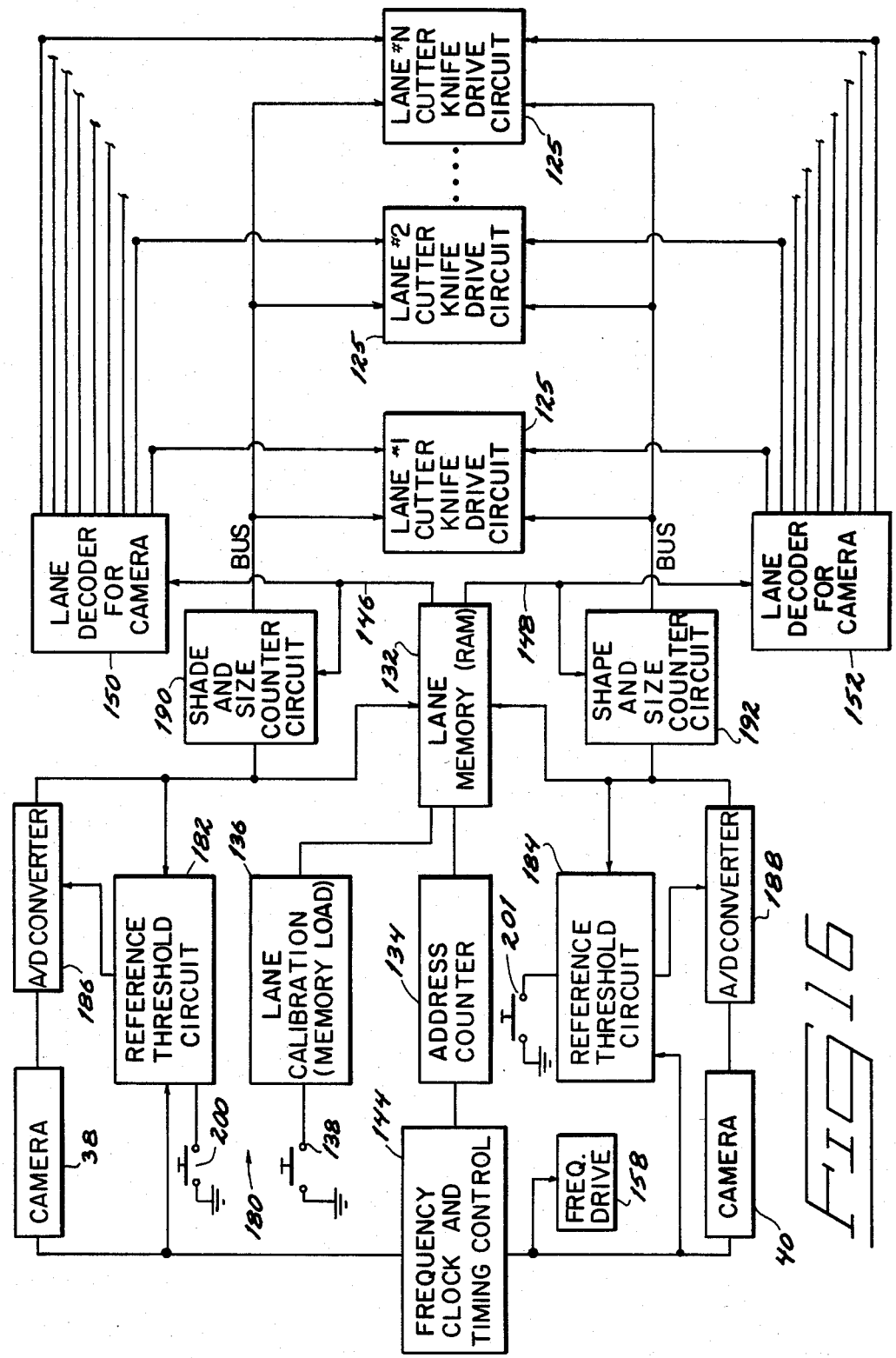
Figure 17:
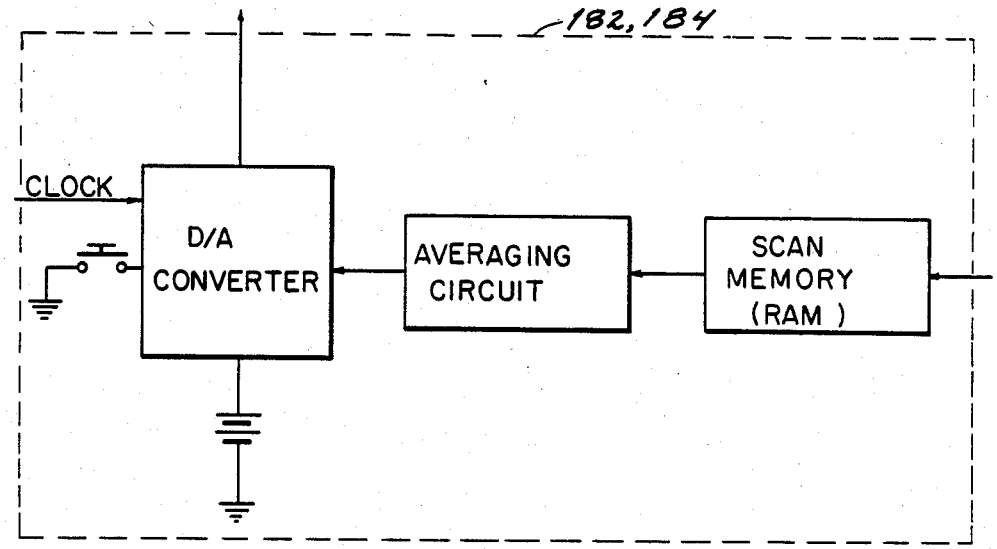
Figure 18:
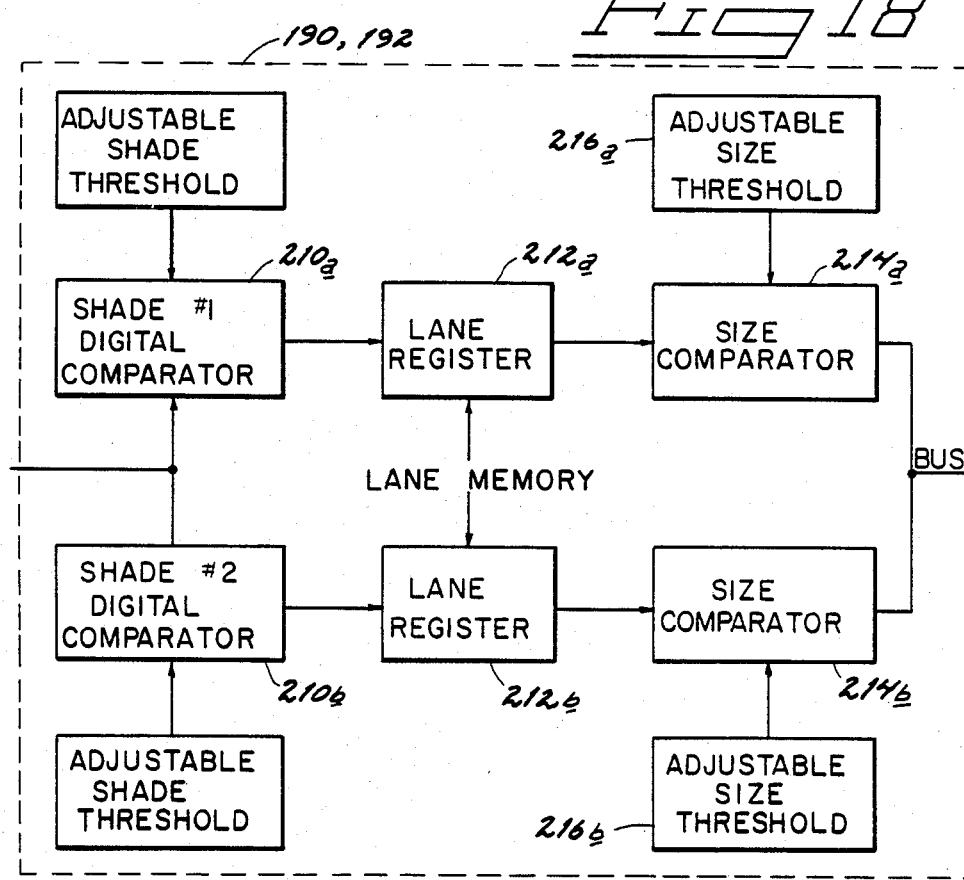

FIGS. 9a–e are a series of sectional views taken along corresponding lines in FIG. 8 illustrating the cross-sectional contour of a cam ring surface of one stationary track member;

FIG. 10 is an isometric view of a knife supporting ring for supporting cutter knives in radial slots formed in the ring;

FIG. 11 is an isometric view of a cutter knife that is utilized in the cutter wheel assembly;

FIG. 12 is a fragmentary transverse cross-sectional view of a portion of a wheel assembly section illustrating an alternative valve system for fluid driving a knife from a retracted position to an extended position;

FIG. 13 is a block diagram of the control system for operating the apparatus illustrating representative functional components for controlling a desired number of cutter knife drive circuits corresponding to the article lanes;

FIG. 14 is a detail view in block diagram of one of the cutter knife drive circuits;

FIG. 15 is a block diagram illustrating a reference threshold circuit;

FIG. 16 is a block diagram of an alternate control system for operating the apparatus;

FIG. 17 is a block diagram illustrating a shade and size control circuit;

FIG. 18 is a schematic of defect signals in relation to threshold levels; and

Figure 20:
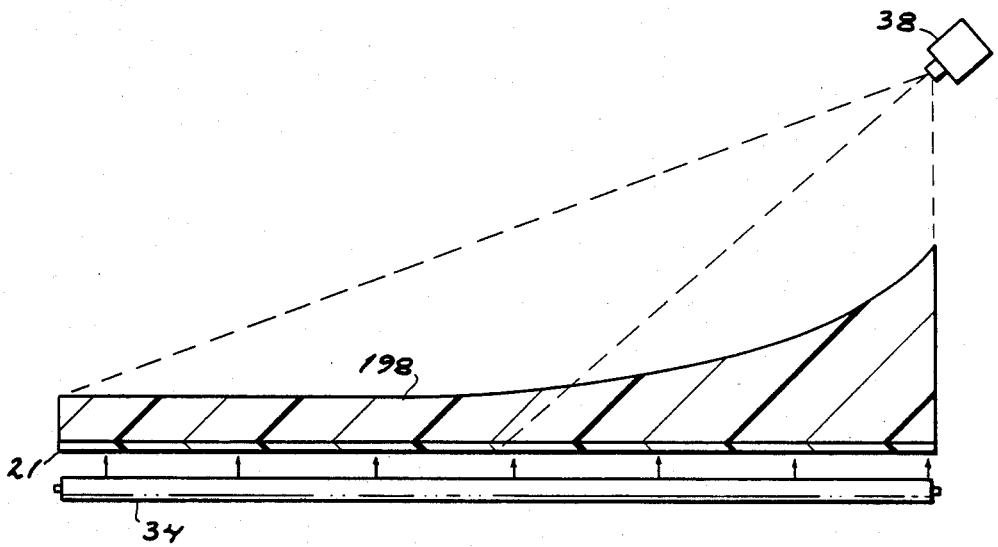

FIG. 20 is a schematic vertical cross-sectional view at the inspection station illustrating the structure and use of a simulated article model.

DETAILED DESCRIPTION OF PREFERRED AND ALTERNATE EMBODIMENTS

The following disclosure is submitted in compliance with the purpose of the United States Constitution "to promote the progress of science and useful arts" (Article I, Section 8).

Referring now in detail to the drawings, there is illustrated in FIGS. 2, 3 and 4 an inspection and cutting apparatus generally designated with the numeral 10 for visually inspecting elongated articles 12 such as raw potato strips or sticks to determine if the articles 12 have shade variation defects 14 therein and for cutting the defect from the article. For raw potato strips or sticks, the shade variation defect 14 is generally caused by a hollow heart, bruising, a residual peel or from heat nacrosic. Such shade variation defects are detrimental to the quality of the product. FIG. 1a shows an elongated article 12 having a shade variation defect 14 therein. FIG. 1b shows the article with the shade variation defect cut into defective sections 16 and 17 to remove the defect from the remainder of the article so as to be able to recover the unaffected portion. Throughout the description, reference will be made to the processing of raw potato sticks or "french fries" for the french fry industry. However, it should be understood that other types of elongated products having shade variation defects or color differentiations may be processed utilizing the same apparatus 10. The apparatus 10 is particularly designed for high volume processing in which even small increases in salvageable product have significant economic benefits.

The inspection and cutting apparatus 10 has a general framework 20 with an elongated article conveyor 21 mounted thereon in which the conveyor 21 extends from a forward end 23 to a rearward end 24. The article conveyor 21 provides a wide moving article support surface 26 between the forward end 23 and the rearward end 24 for receiving the articles with the elongated articles aligned longitudinally in a plurality of transversely spaced lanes as the articles 12 are moved past an inspection station generally designated with the numeral 28 and then past a cutting station generally designated with the numeral 30.

At the inspection station 28, the articles are inspected by an electro-optical inspection means that is radiation sensitive to determine if the articles as they pass the inspection station 28 contain shade variation or color variation defects 14. If the articles contain defects, then the defect 14 is cut from the article by cutting the defect in sections such as 16 and 17 as the articles pass the cutting station 30. The articles that have been processed by the apparatus 10 then may proceed to downstream equipment that separates the defective sections 16 and 17 from the remainder of the sound product.

The electro-optical inspection means includes a radiation generating means such as a lamp bank 34 illustrated in side view in FIGS. 2 and 5 for generating electromagnetic radiation, such as visible light, that is directed onto the wide moving article support surface 26 to illuminate a narrow band or viewing area defined by a narrow slit 36 (FIG. 5) in the lamp bank 34 that extends transversely across the wide moving article support surface 26.

The electro-optical inspection means further includes two scanning cameras 38 and 40 (FIGS. 3 and 4) that are mounted at elevated positions by brackets 41 in which the scanning cameras 38 and 40 are positioned alongside opposite sides of the wide moving article inspection surface and have optical lens axes 42 and 44 respectively that extend downward and inward to the viewing area between the narrow slit 36 with the optical axis 42 and 44 intersecting at a point 46 (FIG. 3) which is below the moving article support surface 26. Preferably each of the scanning cameras 38 and 40 are positioned laterally outward from the edge lane of the articles so that one scanning camera views the top surface and one side of the elongated articles 12 and the other scanning camera views the top surface and the other side surface of the articles as the articles pass through the viewing area in closely packed but spaced lanes.

Preferably each of the scanning cameras 38 and 40 include a linear diode array of photo-electric transducers such as photosensitive diodes for receiving reflected visible radiation generated by the lamp bank 34 in which each of the diodes is focused through a camera lens onto a corresponding viewing area segment (pixel) of the article support surface 26. Each of the scanning cameras 38 and 40 may be purchased as a commercially available product from the Reticon Corporation of Mountain View, Calif. In one configuration, each of the scanning cameras 38 and 40 contain 1,024 photosensitive diodes in which each diode is focused on a distinct viewing area segment (pixel) of the wide moving article support surface 26. Some of the diodes will focus on various portions of the surfaces of the articles as the articles move along the lanes through the viewing area while other diodes will focus on the transverse spaces between the articles defined by the space in between the lanes. Generally the threshold level of the radiant energy does not distinguish between energy from sound article and energy reflected from the support surface 26. However, visible light energy is reflected or transmitted in much different proportion from dark defective spots or area on the elongated potato strip than by the white, sound potato flesh. Generally speaking, a defect surface will reflect or transmit much less visible light energy than does a sound potato surface. Thus, if the amount of received visible light energy is at least a predetermined threshold amount less than the received energy from a sound potato flesh, a defective potato has been detected.

In a preferred embodiment during each scan, each of the diodes (1024) is interrogated to determine the reflected energy level from the corresponding viewing area segments (pixels). It is preferred to have an article support surface moving in excess of 200 feet per minute and to have the scanning cameras 38 and 40 scan the viewing area some 800 scans per second. The scan rate and the surface 26 speed may be adjusted accordingly depending upon many factors including the resolution of the diodes with respect to the amount of illumination from the lamp banks 34.

Although not necessary, it is preferable to synchronize the scanning cameras 38 and 40 to scan the viewing area at the same time so that each scan will occur during a period of uniform density of radiated energy illuminating the viewing area.

Immediately downstream of the inspection station 28 is a cutting station 30 having article cutting means for cutting the defects 14 from the articles after the defects have been detected by the scanning cameras 38 or 40. In a preferred embodiment, the article cutting means includes a cutting wheel assembly 50 that is illustrated in more detail in FIGS. 4–12. The cutting wheel assembly 50 includes a nonrotating hollow axle 52 that extends transversely across the article support surface 26 for supporting a plurality of wheel subassemblies 54 that correspond with the article lanes. Each wheel subassembly is aligned with an article lane for cutting defects from the articles that are detected in the lane. Each wheel subassembly 54 includes a knife support ring 56 (FIGS. 6, 7 and 10) that has an outer periphery 58 that is substantially tangent at its lowest profile with the path of the articles in the corresponding lane. An inner periphery 60 engages and is rotatably slidable on the axle 52. In a preferred embodiment, two adjacent knife support rings 56 form an integral "T"-shaped body 62. The T-shaped body 62 is designed to transversely span and accommodate two lanes. Each side of the body 62 has a plurality of angularly spaced radially oriented knife support grooves 64 formed therein extending from the inner periphery 60 to the outer periphery 58. At desired intervals adjacent the outer periphery 58 of the ring, axial apertures 65 are provided to interconnect the rings 56 across the article surface 26. The number of rings 56 will vary with the number of lanes. One of the important advantages of the apparatus 10 is that the cutting wheel assembly 50 is extremely compact and has a large number of knife support rings 56 to enable the support surface to handle tightly spaced lanes to accommodate a large volume of articles.

Figure 6:
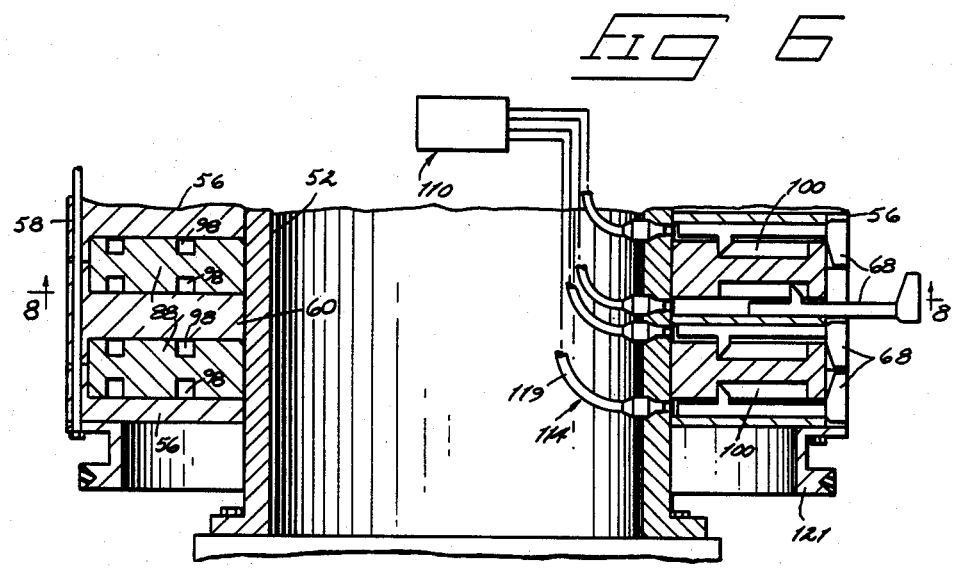
FIG. 6 is a fragmentary axial view taken along line 6—6 in FIG. 5 illustrating a fragmentary portion of a section of the cutting wheel assembly illustrating rotatable rings supporting radially extending knives that are selectively propelled outward by fluid pressure and returned to retracted positions by stationary track members.
Figure 7:
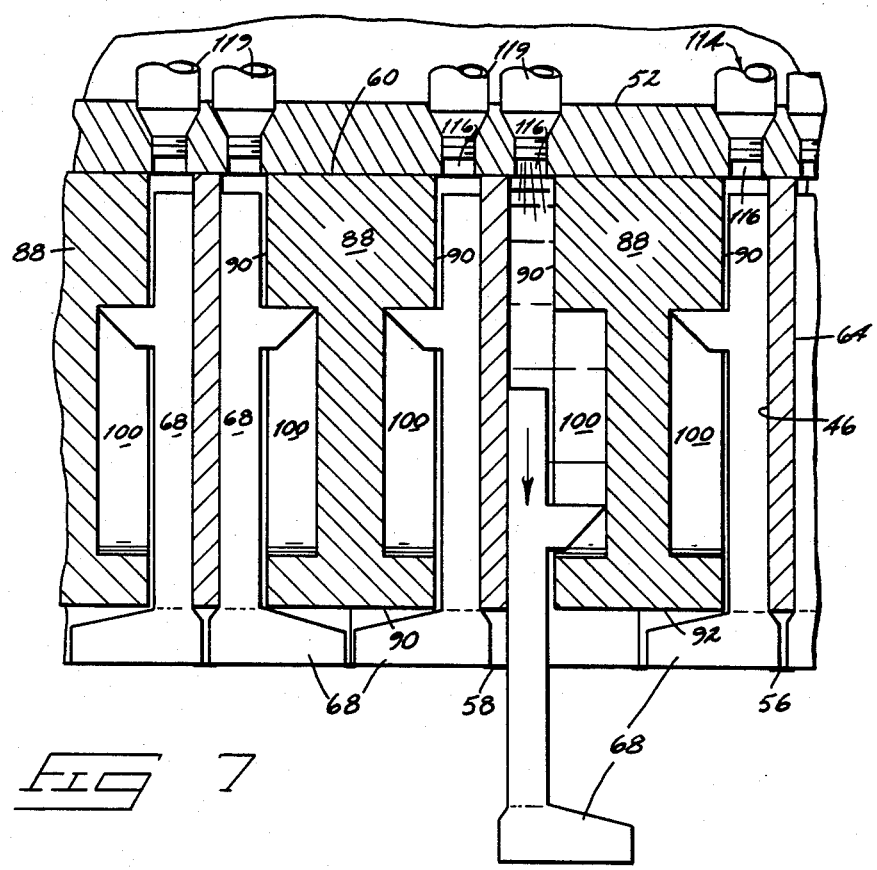
FIG. 7 is an enlarged fragmentary view of a section illustrated in FIG. 6.

Each side of the "T"-shaped body 62 on each ring 56 has an annular cavity 66. Each wheel assembly 54 includes a set of cutter knives 68 that are mounted for free movement radially within the radial knife support grooves 64 as illustrated in FIGS. 6 and 7. A singular knife 68 is illustrated in detail in FIG. 11. Each knife is preferably leg-shaped having a longitudinal leg shaft 80 that rests in a groove 64 with a blade 81 at the foot end thereof that extends laterally outward to one side of the shaft. The blade 81 has a beveled peripheral cutting edge 82. A cam track projection 84 is provided along the shaft 80 that extends outward with the projection 84 coming to an anti-jamming sharp edge or point 86. Each of the cutter knives 68 is designed to move between a retracted non-cutting position in which the blade cutting edge 82 is within the outer periphery 58 and a projecting cutting position illustrated in FIGS. 5, 6 and 7 in which the blade extends beyond to outer periphery 58 for cutting the articles crosswise to form defect sections like sections 16 and 17.

Each of the wheel subassemblies 54 includes a corresponding annular track member 88 that is stationarily mounted on the hollow axle 52. The annular track members 88 are preferably ring shaped and fit within the annular cavities 66 as illustrated in FIGS. 6 and 7. Each annular track ring 88 is designed to assist in the movement of cutting knives in two adjacent lanes. The annular track member 88 includes radial side surfaces 90, an outer periphery 92 and inner periphery 94 that fits on the outside of the axle 52. The axle 52 has an axial slot 86 (FIG. 8) designed to receive key projections 95 formed on the inner periphery 94 of the annular track members 88 to prevent the track members 88 from rotating with the knife support rings 56.

Figure 9:
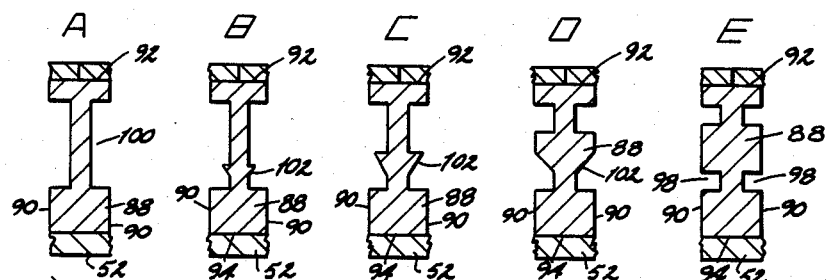

As illustrated in detail in FIGS. 8 and 9, the annular track member 88 is provided on each side 90 with an inner or first annular track or groove 98 that has a substantially constant radius about the axis of the axle 52. The inner annular track 98 extends from a radial opening 100 more than 300° about the axis. The inner annular track 98 has an entrance cam surface 102 that is tapered both axially and radially to minimize the jamming of the cam track projection 84 at the groove opening as the knives are rotated about the axis. The inner annular track 98 is designed to receive the cam track projection 98 when the knives are in the retracted non-cutting position to keep the knives in the non-cutting position as the knives are rotated about the wheel axis. As illustrated in FIGS. 5 and 8, the wheel subassemblies 54 are rotated in a counterclockwise position from approximately a zero angle position in which the knives are substantially horizontal on the back side of the cutting wheel assembly. At the zero angular position, the inner annular track 94 has the radial opening 100 to permit the knives to be moved radially outward from the retracted non-cutting position to the extended cutting position as illustrated in FIG. 8.

Each of the side surfaces 90 of the annular track member 88 further includes an outer second annular track or grooves 104 circumscribing the first annular track and somewhat overlapping the first annular track 98 at the radial opening 100 (FIG. 8). The second annular track 104 has an entrance 106 with an opening 107 at the periphery 92. The entrance 106 has a surface 108 that extends angularly past the radial opening 100 to prevent the track projections from moving outward beyond the second annular track at the radial opening 100. The annular track 104 extends radially about the axis of the cutting wheel assembly 50 to guide and support the cutting knives in the extended cutting position. Throughout most of the annular dimension of the second annular track 104 the cutting knives are held in the cutting position as illustrated in FIGS. 5 and 8. The knives are angularly moved downward into the path of the articles to cut the articles as the knives and articles are moving. After the articles have been cut, the second annular track 108 extends radially inward having an exit 110 communicating with the first annular track 98. The exit 110 has an exit cam surface 111 that moves a projecting knife from the projecting cutting position to the retracted non-cutting position at approximately 310°–320° from the starting position. The opening 107 enables the knives to be automatically loaded and unloaded into the grooves 64 without having to disassemble the wheel subassemblies 54.

The cutting wheel assembly 50 includes knife drive means for moving or pushing the knives outward from the retracted non-cutting position to the extended cutting position at the radial opening 100 or zero degree position. Each wheel subassembly 54 has a knife drive means 114 (FIGS. 6 and 8) axially aligned with respect to cutting knife shafts 70 for directing fluid through an aperture 116 (FIG. 7) formed in the hollow axle 52 for forcing fluid against the end of the knife shaft 70 to direct the knife shaft radially outward in the knife support groove 64 from the retracted position to the extended position. The apertures 116 are positioned through the hollow axle 62 at approximately the zero degree (horizontal) angular location that corresponds with the radial opening 100 in the annular track 98. Each knife drive means includes a fluid line 119 connected to a fluid connector to direct fluid to and through the aperture 116 and against the inner end of the shaft 70 when the blades move past the zero degree. Each wheel subassembly has a corresponding valve means 110 operatively connected to the fluid line 119 for selectively directing fluid through the fluid line and the aperture 116.

In an alternate embodiment illustrated in FIG. 12, the valve means 110 includes a ball valve 112 that is spring loaded for selectively closing the aperture 116. In such a configuration the interior of the hollow axle 52 is pressurized with a fluid so that when the ball valve 112 is retracted from the seat of the aperture 116, the fluid from the pressurized axle 54 is directed outward to drive the blades. Each knife drive means 114 is generally activated for a period of time sufficient to drive or push at least two adjacent blades from the retracted position to the extended position as illustrated in FIG. 8. If the detected defect 14 has a length greater than one section (distance between two blades) then additional blades will be pushed outward to the cutting position.

The cutting wheel assembly 50 includes a drive means for rotating the wheel assemblies 54 in unison to rotate the knife support rings and the sets of cutter knives 68 about the axis of the hollow axle 52. The drive means has a motor 120 (FIG. 4). A pulley rim 121 is mounted to the last knife support ring 56 as illustrated in FIGS. 4–6. The motor 120 rotates the wheel assemblies 54 in unison with the movement of the article support surface 26 so that the peripheral speed of the wheel assemblies 54 coincides substantially with the linear movement of the support surface 26 so that the knives progress downward through the article as the wheel assemblies 54 are rotated so as not to interfere with the longitudinal movement of the articles on the support surface 26 during the severing process.

When the wheel assemblies 54 are driven in the forward position, knives may be inserted radially into empty slots 64 through the opening 107. The knives will automatically then move from the extended position to the retracted position after one revolution. When the wheel assemblies 54 are driven in the reverse direction, it is possible to automatically unload the knives by moving the knives to the extended position. As the knives pass into the opening 107 the knives are cammed outward and can be pulled from the wheel assembly. Consequently new sets of knives may be easily inserted and broken knives may be easily replaced without having to disassemble the cutting wheel assembly.

The inspection and cutting apparatus 10 includes a control means generally designated with the numeral 124 as illustrated in the control schematic in FIG. 13. The control means 124 is connected to a plurality of cutter knife drive circuits to selectively activate the knife drive means in response to the detection of defects by the scanning cameras 38 and 40.

A sample knife drive circuit 125 is illustrated in FIG. 14 having a knife actuating solenoid 130 for selectively operating the knife drive means for the corresponding lane. When a solenoid 130 is activated, fluid is directed through the corresponding aperture 116 to push or drive the knife blades that pass thereby. Each solenoid is activated a sufficient period of time to cause at least two knives to be pushed from the retracted position to the extended position as illustrated in FIG. 8.

The control means 124 includes a coordinating means for coordinating the lane position of a detected defect with a corresponding wheel subassembly 54 and corresponding solenoid 130. The coordinating means utilizes a lane storage memory 132 illustrated in block diagram in FIG. 13. The lane storage memory 132 is preferably a random access memory (RAM) having two channels, each channel corresponding with respective scanning camera 38, 40. Each channel has a number of memory storage elements corresponding to the number of pixels or diodes in the linear array. In the preferred embodiment each camera 38, 40 has 1024 diodes and each channel of the lane storage memory 132 has 1024 storage elements. Each storage element is designed to store information concerning the location and registration of the lanes with respect to the viewing area. Each storage element of the lane storage memory 132 has an address that is addressed by an address counter 134 to sequentially output the lane information from the storage elements in response to the count of the address counter. The address counter counts from 0 to 1023 to identify the address of the memory elements to output the information stored in the storage element on the output line. Initially, it is important to load the lane storage memory 132 with information concerning the lateral location of the lanes and the spaces between the lanes to synchronize or register the lane information with the scanning sequence.

The control means includes a lane calibration means 136 that when activated by memory load pushbutton 138 loads the output from the cameras 38 and 40 into the respective channels of the lane storage memory 132. To preferably accomplish the calibration, a three dimensional lane model is placed in the viewing area with the model having representation of articles positioned at the precise transverse locations with spaces between each article identifying the lane boundaries and then the cameras scan load the memory 132 with the model lane information that corresponds with the viewing area segments. Such a system provides a very easy way of effectively registering the scanning of the cameras with the lanes. Furthermore, it is very easy to adjust the lanes. One merely sets a new model in the viewing area and pushes the memory load button to reload the lane storage memory with the new lane information concerning the location of the articles in the lane and the space between the lanes so that each memory location contains information concerning the lane identification. Consequently, different sized articles and different type articles can be easily accommodated without having to change electronics or reprogram a microprocessor. The address counter 134 addresses each storage element in the same sequence and at the same clock speed as each diode is interrogated so as to synchronize the lane information with the output from the scanning cameras 38 and 40. Camera 38 has an output signal data bus 140 for conveying a serialized train of electrical signals 140 on the data bus in response to the scanning rate in which defect electrical signals appear each time a diode senses a defect. Likewise scanning camera 40 has an output data bus 142 for serially outputting defect information to the lane counter knife drive circuits 125. Each of the lane cutter knife drive circuits receive the signal train from the data buses 140 and 142 as illustrated in FIG. 13.

The control means 124 includes a frequency clock and timing control means 144 that is operatively connected to the cameras 38, 40 for synchronizing the scan rate and the clock rate at which the diodes are interrogated. The frequency clock and timing control means 144 is also connected to the address counter 134 to count the clock pulses to provide address information to the lane storage memory 132 to output the information from the addressed memory element on a lane logic information line 146 or 148 at the same rate that the diodes are being interrogated. The lane logic information placed on the lines 146 and 148 is directed to lane decoders 150 and 152 respectively for decoding the lane logic information to identify the specific lanes being viewed by the scanning cameras. Because of the three dimensional nature of the articles 12 on the support surface 26 and the viewing angle of the cameras 38 and 40, the cameras will probably not be viewing the same lane at the same time. The lane decoders 150 and 152 output signals to respective lane cutter knife drive circuits 125 to indicate the lane that is being viewed. The lane designation is outputted from the lane decoders 152 and 154 on individual lane selection lines that are identified with respect to lane cutter knife drive circuits 125.

Additionally the frequency clock and timing control means 144 is connected to a frequency drive 158 for driving the lamp bank 34 to pulse the lamp bank so that uniform radiation is generated by the lamp bank during each scan. In a preferred embodiment the lamp bank is pulsed at a frequency that is the same or a multiple of the scanning rate up to saturation and is synchronized with the scanning rate so that maximum illumination is generated by the lamp bank during each scan. The signals from the cameras 38 and 40 are directed to AND gates 160 and 162 respectively. Additionally, the lane section lanes are connected to the AND gate 160 and 162. The signals from the lane decoders 150 or 152 are inputted to AND gate 160 and 162 along with data information from the cameras 38 and 40. If the camera senses a defect in an article of a lane being viewed, then signals will appear at both inputs to the AND gates 160, 162. When an output signal appears on one or both of the AND gates 161 or 162 it is directed to an OR gate 165. If a signal is received on either line to the OR gate 165 then an output signal from the OR gate activates electronic switch 167 and in turn activates a solenoid 130. The electrical switch 167 has a timer to maintain activation of the solenoid 130 for a time period sufficient that at least two knives are pushed outward. If a signal remains on the output of either gate 161 or 163, it would indicate that additional defects are detected along the length of the article indicating that additional blades be moved to the extended cutting position. If the entire length of the strip or article 12 is defective, then a sufficient number of blades would be extended to cut the article into multiple sections extending the entire length of the article.

Generally the cameras have internal circuitry for enabling the operator to preset a threshold level representing a minimum radiation level at which electrical signal would be generated indicating that a defect has been detected. The control means 124 further includes a threshold level modifying means for modifying the threshold level at which electrical signals are generated from either camera 38, 40. The threshold level modifying means is designed to dynamically adjust the preset threshold to adapt the system to changing conditions that may occur such as fluctuation in the power voltage to the apparatus and variations in the intensity of the radiation emitted from the lamp bank because of aging of the lamps or from moisture or dirt residing on the face of the lamp bank or on the camera lens that may slightly degrade the amount of radiation received by the diodes. To dynamically adjust the preset threshold level for the cameras 38 and 40, the control means 24 is provided with a real time reference threshold circuit 170 that is illustrated in FIG. 15. To adjust the threshold level, a gray scale target is placed in the viewing area so that one or more of the diodes may be used as reference diodes. Reference location information may be loaded into the memory in the same manner as the lane information. Consequently the reference targets, in addtion to the lanes, are continually scanned to determine if there is any degradation or change in the radiation received by the reference diodes from the reference gray scale target that is placed in the viewing area. In a preferred configuration one of the lane circuits 125a is dedicated and assigned to the reference target and incudes the real time reference threshold circuit 170 (FIG. 15).

The control means has threshold buses connected to the lane cutter knife drive circuits 125 in which the general level of the threshold signal on the bus may be modified by the reference threshold circuit 170. The reference threshold circuit 170 preferably has a charging capacitor 172 with a charging resistor 173 for progressively increasing the level of the signal on the threshold data bus until the threshold reaches the output from the reference diodes in which case the reference electronic switch 167a is activated to close the solenoid switch 177 to discharge or lower the threshold level through discharge resistor 174. When the threshold level is decreased, then the reference diodes will not activate the electronic switch and the voltage begins to build on the threshold bus until the threshold level again indicates to the reference diodes the detection of a defect from the reference target in the viewing area. Such a circuit provides for a simple servo system in which the level continually "hunts" to find the appropriate threshold level depending upon the ambient real time conditions of operation. Should the illumination level decrease then the threshold level will automatically adjust to the new illumination level based upon the amount of reflected energy received by the referenced diodes.

Additionally the threshold level modifying means includes a preset threshold means for each of the lane cutter knife drive circuits 125 so that the camera threshold level is continually adjusted depending upon the distance between the optical axis of the camera and the viewing area segment being viewed by the diodes. It has been found that the reflected illumination received by the diodes is dependent upon the angular distance of the viewing area segment being viewed from the optical axis. The level of radiation relates in relation to the cosine of the off axis angle to the fourth power of the cosine with respect to the angular distance between the optical axis and the viewing segment. Consequently the diodes closer to the optical axis of the camera will receive higher levels of reflected radiation than the diodes that are focused on viewing area segments further away from the optical axis even though the radiation density illuminating the viewing area is relatively constant. Each of the cutter knife drive circuits 125 includes a preset threshold value means 180 and 182 that adjusts the threshold level on a threshold buses during each scan with the threshold level changing from one lane to another to accommodate for the off axis orientation of the viewing diodes with respect to the optical axis of the camera.

Consequently the threshold level modifying means additionally adjusts for the off axis difference in illumination received by the diodes.

An alternate control means 180 is illustrated in FIG. 16 for controlling the operation of the cutter knife drive circuits to selectively activate the knife drive means in response to the detection of selected defects by the scanning cameras 38 and 40. Control means 180 incorporates unique reference thresholds 182, 184; analog-to-digital signal generators (convertors) 186, 188 and shade and size control circuits 190, 192. Each of the transducers (diodes) of the scanning cameras 38, 40 produce analog electrical representation of the magnitude of the radiation received by the transducer. The analog electrical representations are serially fed from the cameras 38, 40 to analog-to-digital signal generators or convertors 186, 188 respectively in synchronization with the scanning rate. The analog electrical representations are compared with a reference thereshold level generated by reference threshold circuits 182, 184.

Figure 19:
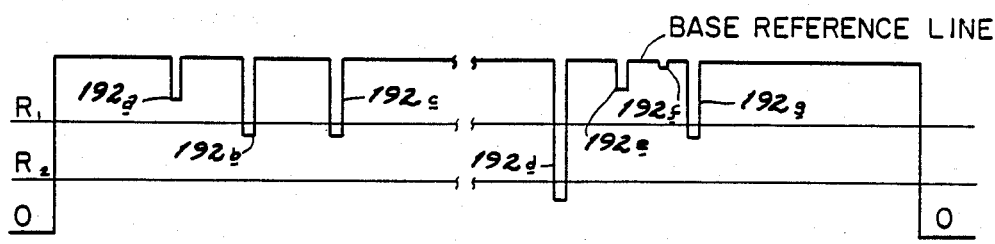

The signal generators 186, 188 then generate digital signals representing the value of the difference between the reference threshold level and the analog electrical representations from the transducers. Analog representation 192 of the generated digital signals are illustrated in FIG. 19.

The reference threshold level is initially established during a calibration cycle. It is intended that the reference threshold level vary with each transducer or pixel having a reference threshold level that is unique to the location and geometry of the pixel and to the articles being inspected. In this embodiment an article calibration model 198 is used in the production of the reference threshold level. As shown in FIG. 20, the conveyor 21 is preferably constructed of a translucent material that permits the transmission of light from beneath the conveyor. The light source 34 in this embodiment is mounted immediately beneath the conveyor 21.

The article calibration model 198 is likewise translucent and is made of a material that transmits light energy similarly to the article being inspected. For potato slices (french fries) the model is made of a milky white plastic material representing white potato flesh. The model 198 has a thickness that varies from one side to the other to compensate for the varying distances and angles with respect to the camera 38. A different model 198 may be constructed for different kinds or types of articles so that reference threshold level has a base value that is unique to the articles being inspected.

During the calibration cycle the model 198 is placed across the viewing area with the thick side closest the camera being calibrated. Then the calibration button 200, 201 is pushed to start the calibration or "dynamic learning" of the reference threshold circuit.

During calibration the activated camera scans the model 198 without the articles and the signal generators generate digital signals 186 and 188 that are stored in a scan memory unit (RAM) 204, 205. In a preferred embodiment, the scan memory units 204, 205 have sufficient capacity for storing digital signals for more than one scan. The digital signals are then averaged by averaging circuit 206, 207 to obtain an average digital signal for each transducer or pixel. The averaged digital signal is then processed by a digital-to-analog signal generator or convertor 208, 209 to generate an analog reference threshold level that is applied in a feed-back loop to the signal generators 186, 188. The net result is that the reference threshold level subtracts or calibrates out variations in illumination, vignetting and other factors and provides a "flat" light across the viewing area and establishes a shade base line that is unique to the articles being inspected. The flat base line for white flesh potatoes is illustrated in FIG. 19.

After the calibration is completed, the model 198 is removed and the apparatus is ready to receive articles. From then on the digital signals generated by signal generators 186, 188 represent the difference of the shade of the article as observed with that of a desired reference shade of the article independently of other factors such as the location and geometry of the article with respect to the camera and variations of illumination across the viewing area and other factors.

The digital signals generated from the generators 186, 188 are directed to the shade and size control circuits 190, 192 respectively to determine if a cut signal should be generated to activate the cutter knife drive circuits 125. Each shade and size control circuit 190, 192 has one or more shade comparators 210 for comparing the digital signal with a reference defect shade signal. In the embodiment illustrated in FIG. 16, two comparators 210a and 210b are provided for each camera which are set at different levels. One comparator 210a is set to trigger an output signal when the camera detects a "light" defect such as a blemish and the other comparator 210b is set to trigger an output signal only when the camera detects a dark spot. Adjustable shade threshold circuits are connected to the comparators to provide adjustable thresholds. FIG. 19 illustrates a shade #1 threshold level $R_1$ to generate an output when a light defect (192b, c, d, and g) is detected and a shade #2 threshold level $R_2$ to generate an output when a dark defect is detected. A dark defect will trigger both comparators 210a and 210b to generate output signals.

The output signals from the comparators 210a and 210b are directed to lane registers 212a and 212b respectively. The output signals from the comparators 210a and b are directed to the appropriate lane register 212 under the control of the lane memory circuit 132 so that each lane register 212 will only count output signals that are associated with articles in their particular lane.

The lane registers 212a and b are continually monitored by size comparator circuits 214a and b respectively for generating cut signals when the defect count for a particular lane exceeds a preset count value. The count values are adjustable and set by adjustable size threshold circuits 216a and b respectively. In this manner the count in each lane register represents the size of the article defect which is compared against a preset size for deciding whether to cut the defect from the article. For many applications it may be desirable to remove "light" defects only if the defect size is large; whereas it may be desirable to remove small area defects that are "dark".

By adjusting the shade threshold circuits and the size threshold circuits, one is able to vary the shade and size of the defects to be cut from the articles.

The generation of a cut signal by its size comparator circuits 214a or 214b is placed on the data bus to the cutter knife drive circuits as illustrated in FIG. 16. The cut signal is gated by the AND gates 160, 162 in synchronization with the lane select signal to activate the appropriate lane solenoid 130.

The operation of the apparatus may be generally explained with respect to FIG. 5 showing a lane of in-line articles passing the viewing area at the inspection station 28. When a defect is detected an output signal is generated by the sensing camera on the respective data bus. Additionally, segment information concerning the specific lane being interrogated is sent to the lane decoders 150, 152 for activating the corresponding cutter knife drive circuit. If a cut signal is generated, then the respective AND gate 160, 162 is activated to energize the solenoid that operates the corresponding knife drive means. Fluid pressure is directed against the knives at the zero degree location to drive the knives outward to the projected position illustrated in FIG. 5. The electronic switch 167 has a sufficient dwell time so that at least two knives are projected when a defect is sensed. The knives are projected at the zero location and then move upward and over and then downward at the same rate that the articles move on the conveyor surface 26. Two knives are shown being moved to the projected position in view of a defect being sensed as it passes through the viewing area. The distance between the inspection station 28 and the cutting station 30 may be adjusted so that the knife will intersect and cut the article at the location where the defect occurs. Preferably, the peripheral distance from the zero position to the position in which the periphery of the cutting wheel is tangent to the path of the articles corresponds to the distance between the axis of the cutting wheel and the viewing area in the inspection station 28. Additionally the speed of the periphery of the cutting wheel assembly 50 corresponds with the linear speed of the support surface 26. Although not shown, the position of the cutting wheel may be adjusted slightly either forward or back to fine tune the actuation of the knives to the extended position in relation to their movement about the wheel until they intersect the path of the articles to accurately dissect the articles to remove the defective sections as illustrated in FIG. 1B.

Because of rather large clearances the fluid from the knife drive means flows out the slots 64 to the periphery 58 to lubricate the knives and prevent the knives from picking up the cut sections.

In compliance with the patent law statutes, the invention has been described in language more or less specific as to structural features. It is to be understood, however, that the invention is not limited to the specific features shown, since the means and construction therein disclosed comprises a preferred form of putting the invention into effect. The invention is therefore claimed in any of its forms or modifications within the proper scope of the appended claims, appropriately interpreted in accordance with the doctrine of equivalents.

I claim:

1. Inspection and cutting apparatus for inspecting elongated articles to detect shade variation defects in the articles and for cutting one or more sections from the articles to remove the detected defects from the articles, comprising:

an article conveyor having a plurality of transversely spaced conveying lanes for receiving the elongated articles and moving the elongated articles single file in a plurality of transversely spaced lanes successively past an inspection station and a cutting station;

an electro-optical inspection means positioned at the inspection station for viewing the articles as the articles move through the viewing area at the inspection station and for generating electrical signals when defects are observed in which the signals are characteristic of the defects;

a cutting wheel assembly positioned at the cutting station at a selected downstream distance from the inspection station;

said cutting wheel assembly having a plurality of knife support rings aligned with the conveying lanes and mounted for rotational movement about a transverse axis in which the knife support rings have a periphery that moves in a circular path that is substantially tangent to the path of the articles;

said cutting wheel assembly having a set of cutter knives mounted for radial movement on each knife support ring at angularly spaced increments about the transverse axis for radial movement between retracted noncutting positions and extended cutting positions;

said cutting wheel assembly having a knife positioning means for selectively directing a fluid against the knife at a preselected angular position to push the knife radially outward from the retracted noncutting position to the extended cutting position;

drive means operatively connected to the knife support ring and responsive to the article conveyor for rotating the knife support ring in a forward direction about a transverse axis in coordination with the movement of the articles to synchronize the movement of the knives past the preselected angular position of the knife drive means in relation to the movement of the articles past the cutting station;

said cutting wheel assembly having track means for receiving the cutter knives when the cutter knives are in the extended cutting positions and for maintaining the cutter knives in the extended cutting position without the air of fluid as the knives move from the preselected angular position past the cutting station to cut the articles; and control means operatively connected to the electro-optical inspection means for sensing the generation of the electrical signals and in response thereto selectively activating the knife positioning means to direct fluid against selected knives as the knives move past the preselected angular position of the knife drive means to push the selected knives outward to their extended cutting positions to enable the cutting track means to maintain the cutter knives in the extended cutting position to cut the sections containing the defects from the articles as the projected knives are progressively moved into the path of corresponding articles moving past the cutting station.

2. The inspection and cutting apparatus of claim 1 wherein the electro-optical inspection means includes a scanning camera for repeatedly scanning the viewing area transversely across the conveying lanes as the elongated articles move through the viewing area and for generating the electrical signals when defects are viewed during such scanning.

3. The inspection and cutting apparatus of claim 2 wherein the scanning camera has an array of photo electric diodes for receiving reflected radiant energy through a viewing lens having an optical axis and wherein the electro-optical inspection means includes mounting means for mounting the scanning camera above the article conveyor with the optical axis directed downward intersecting the viewing area and the array of photo-electric diodes focused transversely across the conveying lanes with each photo electric diode focused on a corresponding transverse segment of the viewing area.

4. The inspection and cutting apparatus of claim 3 wherein the control means includes:
  (a) memory storage means having a number of storage elements corresponding to the number of viewing area segments;
  (b) lane registration means for loading lane identification logic information into the storage elements corresponding with the viewing area segments in relationship to the location of the lanes with respect to the viewing area segments;
  (c) memory read means for reading out the lane logic information;
  (d) timing means operatively connected to the scanning camera and the memory read means for synchronizing the scanning of the viewing area with reading out of the lane logic information; and
  (e) logic means responsive to the generation of the electrical signals from scanning camera and the reading out of the lane logic information for activating the corresponding knife drive means associated with the lane of a scanned defective article to cut the defective section from the scanned defective article as the article moves past the cutting station.

5. The inspection and cutting apparatus of claim 1 wherein the electro-optical inspection means includes an electric lamp bank extending transversely across the article conveyor overlying the lanes at the inspection station with a plurality of electric lamps directly above the paths of the articles and wherein the control means includes means for electrically pulsing the electric lamps at a frequency equal to or greater than the rate at which the viewing area is repeatedly scanned to direct substantially uniform radiation onto the viewing area while the viewing area is being scanned.

6. The inspection and cutting apparatus of claim 1 wherein each of the articles have a top surface and opposite side surfaces and wherein the electro-optical inspection means includes two scanning cameras mounted adjacent opposite sides of the article conveyor that are directed downward and inward for repeatedly scanning the viewing area transversely across the conveying lanes with one scanning camera viewing the top surface and one side surface of the articles in the viewing area and the other scanning camera viewing the top surface and the other side surface of the articles in the viewing area during each scan for generating electrical signals when defects are observed on the viewed surfaces.

7. The inspection and cutting apparatus of claim 6 wherein the control means has coordinating means operatively connected to the two scanning cameras for synchronizing the scanning of the two cameras and for activating the corresponding knife drive means associated with the lane in which a scanned defective article is observed by either camera.

8. The inspection and cutting apparatus of claim 7 wherein the coordinating means includes:
  (a) memory storage means having a number of storage elements associated with each camera corresponding to a prescribed number of angular increments of the viewing area as viewed by each camera;
  (b) lane registration means for loading lane identification logic information into the number of storage elements in relationship to the lateral location of the lanes with respect to the angular increments;
  (c) memory read means for reading out the lane logic information;
  (d) timing means operatively connected to the scanning cameras and the memory read means for synchronizing the scanning of the viewing area by both cameras and the read out of the lane logic information; and
  (e) logic means responsive to the generation of the electrical signals from the scanning cameras and the reading out of the lane logic information for activating the corresponding knife drive means associated with the lanes in which the defective articles are viewed to cut defective sections from the defective articles as the articles move past the cutting station.

9. The inspection and cutting apparatus of claim 1 wherein each cutter knife has a track follower; and wherein the track means includes a stationary track member associated with each knife support ring having (1) a first annular track extending partially about the transverse axis from the angular position of the knife drive means for engaging the track follower of those knives in the retracted noncutting position and maintaining such knives in the retracted noncutting position as the knife support ring is rotated about the transverse axis, and (2) a second annular track extending partially about the transverse axis from the angular position of the knife drive means for engaging the track follower of those knives pushed to the extended, cutting position and maintaining such knives in the extended cutting position as the extended knives cut the defective articles.

10. The inspection and cutting apparatus of claim 9 wherein the knives are movably mounted on the knife support ring for free movement radially on the knife support ring and wherein the second track has a track entrance surface angularly overlapping the angular position of the knife drive means for preventing the radial removal of the knives from the knife support ring when the knife support ring is rotated in a forward direction and for permitting the radial removal of the knives from the knife support ring when the knife support ring is rotated in a reverse direction to enable the knives to be easily loaded and unloaded from the cutting wheel assembly without disassembling the cutting wheel assembly.

11. The inspection and cutting apparatus of claim 1 wherein the knife drive means includes a fluid aperture at the angular location directly opposing inner ends of the knives as the knives pass the angular location for directing a fluid against the inner ends of the knives to push the knives radially outward from the retracted noncutting position to the projected cutting position.

12. The inspection and cutting apparatus of claim 1 wherein each knife drive means includes a plurality of laterally spaced fluid apertures at the angular position associated with the corresponding knife support rings for directing fluid against inner ends of the knives to push the knives radially outward from the retracted noncutting position to the projected cutting position.

13. The inspection and cutting apparatus of claim 12 wherein the laterally spaced fluid apertures are interconnected by a common pressurized fluid manifold and wherein the knife drive means includes valve means associated with corresponding fluid apertures and wherein the control means is operatively connected to the valve means for selectively opening and closing the valve means to selectively push the knives from the retracted noncutting position to the projected cutting position.

14. The inspection and cutting apparatus of claim 1 wherein the control means includes size means responsive to the generation of the electrical signals associated with corresponding lanes for determining the size of a defect and for activating the cutting means when the determined defect size exceeds a preset value.

15. The inspection and cutting apparatus of claim 14 wherein the size means includes a counting means corresponding with each lane for counting the number of electrical signals generated by defects in the articles located in each lane during a plurality of scans and for generating a cut signal when the accumulated number exceeds the preset value.

16. The inspection and cutting apparatus of claim 1 wherein the control means includes shade means for determining defects having different shades and size means for determining the size of the different shade defects and summary means operatively connected to the article cutting means for cutting varying shade and size defects from the articles.

17. The inspection and cutting apparatus of claim 16 wherein the control means has adjusting means for adjusting threshold levels of the shade means and the size means to enable the apparatus to change the shade and size of the defects to be cut from the articles.

18. The inspection and cutting apparatus as defined in claim 17 wherein the second track has a track entrance communicating with the first track and wherein the track means includes a cam track projection terminating in a sharp edge to prevent a knife from jamming in the track entrance.

19. The inspection apparatus of claim 16 wherein the control means has adjusting means for adjusting threshold levels of the shade means and the size means to enable the apparatus to determine the shade and size of the defects in the articles.

* * * * *